(12) United States Patent
Mannschedel

(10) Patent No.: US 6,902,399 B2
(45) Date of Patent: Jun. 7, 2005

(54) CLEANING INSTRUMENT FOR A TOOTH ROOT CANAL

(75) Inventor: Werner Mannschedel, Langenau (DE)

(73) Assignee: Roeko GmbH & Co. KG, Langenau (DE)

( * ) Notice: Subject to any disclaimer, the term of this patent is extended or adjusted under 35 U.S.C. 154(b) by 102 days.

(21) Appl. No.: 10/140,792

(22) Filed: May 7, 2002

(65) Prior Publication Data

US 2002/0172922 A1 Nov. 21, 2002

(30) Foreign Application Priority Data

May 16, 2001 (DE) .......................... 101 23 814

(51) Int. Cl.⁷ .............................................. A61C 15/00
(52) U.S. Cl. .................. 433/141; 433/102; 433/224; 132/329
(58) Field of Search ................ 433/81, 141, 216, 433/224, 102; 132/321, 329

(56) References Cited

U.S. PATENT DOCUMENTS

| | | | | |
|---|---|---|---|---|
| 1,840,484 A | * | 1/1932 | Brown ........................ 15/188 |
| 4,280,518 A | * | 7/1981 | Gambaro ..................... 132/323 |
| 4,449,933 A | * | 5/1984 | Forni .......................... 433/141 |
| 4,832,061 A | * | 5/1989 | Hwang ........................ 132/329 |
| 4,911,187 A | | 3/1990 | Castillo ....................... 132/321 |
| 5,775,346 A | * | 7/1998 | Szyszkowski ............... 132/329 |
| 5,899,693 A | * | 5/1999 | Himeno et al. ............. 433/119 |
| 6,082,999 A | * | 7/2000 | Tcherny et al. ............... 433/80 |
| 6,085,761 A | * | 7/2000 | Inaba .......................... 132/329 |
| 6,179,617 B1 | * | 1/2001 | Ruddle ........................ 433/224 |
| D441,141 S | * | 4/2001 | Shalita ........................ D28/65 |
| 6,343,929 B1 | * | 2/2002 | Fischer ......................... 433/81 |
| 6,468,080 B1 | * | 10/2002 | Fischer et al. .............. 433/149 |

* cited by examiner

*Primary Examiner*—Ralph A. Lewis
(74) *Attorney, Agent, or Firm*—Frommer Lawrence & Haug LLP; Ronald R. Santucci

(57) ABSTRACT

The cleaning instrument (10) comprises a head portion (10) and, adjacent thereto, a cleaning portion (14) having a shank (20), which is provided with bristles (22) on its external surface. In order that especially the tooth root canal or also a tooth interstice can be reliably cleaned using the cleaning instrument (10), the shank (20) is of integral construction with the bristles (22).

17 Claims, 1 Drawing Sheet

CLEANING INSTRUMENT FOR A TOOTH ROOT CANAL

BACKGROUND TO THE INVENTION

The invention relates to a cleaning instrument for a tooth root canal and also for a tooth interstice, comprising a head portion and, adjacent thereto, a cleaning portion having a shank provided with bristles on its external surface. The invention relates also to a method of producing a cleaning instrument for a tooth root canal, which instrument comprises a head portion and, adjacent thereto, a cleaning portion having a shank the external surface of which is provided with bristles.

Cleaning instruments of that kind are used in the course of dentistry treatments after the root canal of a tooth has been prepared using an appropriate reaming or drilling instrument.

The object of cleaning is to remove, from the tooth, material that, on clearing out, remains behind in the tooth root canal, so that the tooth root canal can subsequently be filled.

In conventional cleaning methods, a rinsing solution intended to take up and remove the remaining material is introduced into the tooth root canal. However, such methods do not ensure that material which has gathered at the end of the root canal, that is to say in the apical region, is also rinsed out from the root canal.

Alternatively or additionally, tooth root canals can be cleaned with rotating, so-called "drilling", instruments. However, not every tooth root canal is of circular cross-section, so that it is not possible for all regions of the tooth root canal to be cleaned using such instruments.

Brushes in which bristles are bound into wound wires are known for cleaning cavities and drilled holes in teeth. Such brushes are, however, usually too large to be able to clean a tooth root canal. Furthermore, during rotation of the brush, the wound wires can twist open and bristles can come away and remain behind in the root canal.

PROBLEM UNDERLYING THE INVENTION

The problem underlying the invention is to provide a cleaning instrument and a method overcoming the previously mentioned disadvantages and especially allowing the tooth root canal to be cleaned reliably.

SOLUTION ACCORDING TO THE INVENTION

The problem is solved in accordance with the invention by a cleaning instrument of the kind mentioned at the beginning in which the shank is of integral construction with the bristles. The problem is also solved by a method of the kind mentioned at the beginning in which the shank is produced integrally with the bristles.

The cleaning portion of a cleaning means described at the beginning must be so arranged that the shank holds the bristles securely, and, at the same time, the rotary motion is transferred from the head portion of the cleaning instrument to the tip of the cleaning portion. Accordingly, the shank must not twist substantially during cleaning; it is therefore of relatively rigid construction.

The bristles, on the other hand, must not damage the wall of the root canal. They must be in contact with the wall and must conform thereto. Bristles are therefore made from a relatively soft material or are made very fine, with a small diameter.

Despite those considerations, in the case of the invention, the shank and the bristles are of integral construction, which means that they are produced in the form of a single workpiece, that is also to say, usually, from one material. That has the advantage that the bristles are joined to the shank in considerably better manner. They therefore do not come away during cleaning.

Furthermore, almost any desired form can be given to the bristles; they do not need to be bound into wound wires. Production is simpler and more economical. Moreover, the bristles can be made especially small, in the form of so-called micro-bristles, which is not possible in the case of conventional production methods for cleaning brushes for tooth apertures because very small bristles immediately come away from the combination of wound wires.

Overall, the bristles can form any desired brush shape. Accordingly, such a cleaning brush can, for example, also be of oval cross-section.

In order to achieve adequate rigidity of the shank, the latter can be of relatively thick construction because the bristles can, in accordance with the invention, be made especially short.

Overall, the diameter of the cleaning portion of the cleaning instruments according to the invention can be made smaller than in conventional brushes. The cleaning instruments are therefore outstandingly suitable for cleaning root canals. Compared to conventional rinsing methods, they lead to a considerably better cleaning result.

ADVANTAGEOUS DEVELOPMENTS OF THE INVENTION

In an advantageous development of the cleaning instrument according to the invention, the shank, together with the bristles, is produced by a milling method, especially a micro-milling method. Because milling is a material-removing method, the bristles can be made sharp-edged using this method, so that they clean especially well. The bristles can, moreover, be given any desired shape. Milling is recommended when relatively rigid or stiff basic material is used.

Alternatively or additionally, the shank and bristles can be produced by a moulding method, especially a micro-injection-moulding method. Such a method is especially economical. It is especially advantageous when relatively soft basic material is employed because, in the moulding process, the entire mould, that is to say especially the bristle cavities of the mould, is filled by the basic material especially well.

In order to increase the torsional rigidity and bending rigidity of the shank of the cleaning instrument according to the invention, the shank can advantageously be provided with a core made from a stiffening material, especially metal. The cleaning portion of the instrument according to the invention is usually made from plastics material. It is possible, either in a prior operation or during the actual micro-moulding method, for a rod of metal, for example of titanium or high-quality steel, of fibre-glass or of carbon to be incorporated in the moulded plastics material. Suitable plastics materials are especially polypropylene, polystyrene or elastomers. Such plastics materials are especially suitable because, on the one hand, the bristles do not come away from, that is to say do not tear off, the shank and, on the other hand, they conform to the contour and surface of the root canal. The core arranged in the shank also facilitates the attachment of a head portion, which either can have a hand grip or is intended for insertion into a drilling device.

In order to obtain optimum cleaning action and, at the same time, high stability for the cleaning portion, the bristles overall form a substantially conical outer shape. Such a shape ensures that the force is directed from the head portion of the cleaning instrument to the tip of the cleaning portion without substantial twisting of the shank. At the same time, the bristles are required to conform relatively little to the cleared root canal, which usually becomes narrower at least in steps. The conical outer shape advantageously has a diameter of from 0.4 mm to 2.0 mm at the head portion and a diameter of from 0.1 mm to 1.0 mm at the tip. The bristles are advantageously in the form of round bristles having a diameter of 0.01 mm.

The cleaning instrument according to the invention carries material out from the root canal especially well when the bristles are distributed over the outer surface of the shank in a helical arrangement. The cleaning instrument then moves material in the manner of a drill without, however, enlarging the root canal. By appropriately selecting the hardness, shape and position of the bristles, the cleaning action can be appositely matched to prevailing requirements. In the process, different cleaning regions having differently formed bristles or having bristles made from different materials can be distributed over the shank.

In advantageous developments of the cleaning instrument according to the invention, for further improvement of the cleaning result, the bristles are coated. They are provided especially with an abrasive material or a chemically acting agent, for example a lubricating agent or a disinfecting agent.

In order that material at the end of the root canal, that is to say in the apical region, also can be removed using the cleaning instrument according to the invention, the bristles are advantageously arranged, at least in part, inclined towards the longitudinal axis of the shank; at the tip of the shank, bristles especially project out from the shank in substantially the same direction as the longitudinal axis of the shank.

BRIEF DESCRIPTION OF THE DRAWING

An embodiment of a cleaning instrument according to the invention is illustrated in further detail hereinafter with reference to the annexed diagrammatic drawing, in which.

DETAILED DESCRIPTION OF THE EMBODIMENT

Figure 1:
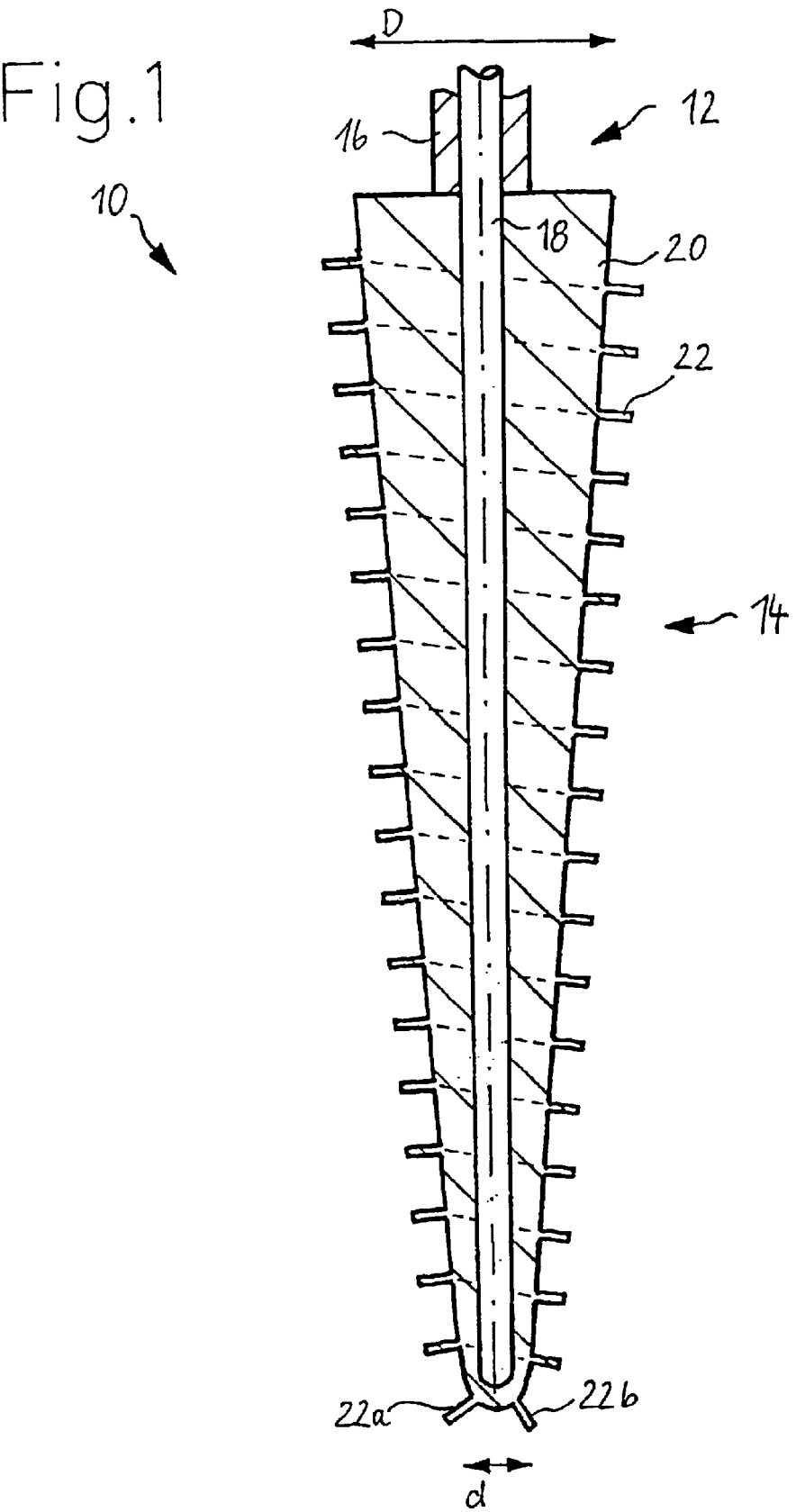
FIG. 1 is a longitudinal section through an embodiment of a cleaning instrument according to the invention.

A cleaning instrument 10 shown in FIG. 1 has a head portion 12 and, adjacent thereto, a cleaning portion 14. The cleaning instrument 10 is used for removing, from a tooth root canal, material that has remained behind in the tooth root canal after the latter has been cleared out using a drilling or scraping instrument. It is furthermore possible, using the cleaning instrument 10, also to clean regions of the tooth root canal that cannot be cleaned using drilling instruments. In FIG. 1, the cleaning instrument 10 is not shown true to scale but rather, for the purpose of better representation, in greatly shortened form.

The head portion 12 is formed substantially by a sleeve 16, which can be fixed in a drill chuck of a drilling or cleaning device (not shown). In an alternative embodiment (not shown), the head portion 12 has a hand grip, by means of which the cleaning instrument 10 can be introduced into a tooth root canal manually and moved, especially rotated, therein.

Arranged in the sleeve 16 is a core 18 in the form of a metal rod made from titanium. The sleeve 16 and the core 18 are connected by means of a press fit. Alternatively or additionally to such a non-positive connection, a positive connection can be provided, for example by providing the upper (in relation to FIG. 1) end portion of the core 18 with a polygonal cross-section.

The core 18 is in the form of a cylindrical rod, that is to say it has substantially the same diameter over its entire length. In the embodiment shown, the diameter is 0.08 mm. Alternatively, the diameter can advantageously be about from 0.05 mm to 0.8 mm.

The core 18 extends into a shank 20, which has a substantially conical shape and which surrounds the core 18 symmetrically. The cone has a diameter D of 0.4 mm at its upper (in relation to FIG. 1) end and a diameter d of 0.1 mm at its opposite end. The shank 20 is provided with narrowing of about 0.04 mm per mm of length in a longitudinal direction. In alternative embodiments (not shown), the narrowing is about from 0.02 mm per mm of length in a longitudinal direction to 0.06 mm per mm of length in a longitudinal direction.

The shank 20 is made from plastics material, which has been moulded around the core 18 by means of a micro-injection-moulding method. By that means, a lasting connection is created between the core 18 and the shank 20. In the present embodiment, polypropylene has been used.

In an embodiment that is not shown, the core 18 is of slightly conical shape, that end region of the cone which tapers towards a point being located at that end of the core 18 which is arranged opposite the head portion 12. A core 18 of such a conical shape is easier to bend in the end region which tapers towards a point than in the head portion 12. During insertion into, and cleaning of, the tooth root canal, the shank 20 therefore conforms more readily to the shape of the tooth root canal in the latter's end region, where the tooth root canal is usually curved.

On the outer surface of the conical shank 20 there are formed bristles or knobs 22, which are arranged along a helical line indicated by a broken line in FIG. 1. The bristles 22 protrude from the outer surface of the conical shank 20 in a substantially perpendicular direction. They are about 0.05 mm long and have a diameter of 0.01 mm. In alternative embodiments (not shown), the bristles 22 are from 0.02 mm to 0.2 mm long.

At the lower (in relation to FIG. 1) end of the shank 20, that is to say at the end arranged opposite the head portion 12, there are arranged on the shank 20 bristles 22a and 22b, which also point in the direction of the longitudinal axis of the shank 20.

The cleaning instrument 10 is fixed into the said drilling device and is introduced, with rotation, into a previously cleared tooth root canal. In the process, the bristles 22a and 22b co-operate with the bristles 22 and together with the latter they carry out material even from the apical portion of the tooth root canal.

The bristles 22, 22a and 22b are produced together with the shank 20 in a single micro-injection-moulding method. The bristles 22, 22a and 22b are consequently lastingly connected to the shank 20.

At the same time, the bristles 22, 22a and 22b are sufficiently soft for them to conform readily to the wall of the root canal.

In an embodiment (not shown) of a cleaning instrument 10, the shank 20 of the cleaning portion 14 is cylindrical and the bristles 22 formed thereon form a conical shape that approximately corresponds to the conical shape shown in FIG. 1. In a cleaning instrument 10 of that kind, the bristles 22 are especially long especially in the region located near the head portion 12. At the same time, the shank 20 is also especially slender in that portion. A cleaning instrument 10 of such a form can accordingly also be inserted into especially narrow root canals. The comparatively long bristles 22 also readily conform to the wall of such a narrow root canal.

In order to increase further the cleaning action of the cleaning portion 14, the bristles 22, 22a and 22b are coated with an abrasive material. Alternatively or additionally, a lubricating and/or disinfecting agent can be applied to the bristles 22, 22a and 22b.

List of Reference Symbols
10 cleaning instrument
12 head portion
14 cleaning portion
16 sleeve
18 core
20 shank
22 bristles
22a bristle at the tip
22b bristle at the tip
D diameter at the head portion
d diameter at the tip

What is claimed is:

1. A cleaning instrument (10) for a tooth root canal or tooth interstice, comprising a head portion (12) and, adjacent thereto, a cleaning portion (14) having a shank (20) provided with bristles (22) on its external surface, the shank having a longitudinal axis, wherein the shank (20) is of integral construction with the bristles (22), and has a core (18) made from a stiffening material, wherein the shank (20) has a substantially conical shape and which symmetrically surrounds the core (18), and wherein the bristles (22) are arranged, at least in part, inclined towards the longitudinal axis of the shank and wherein the bristles (22) protrude from the shank (20) in a substantially perpendicular direction.

2. The cleaning instrument according to claim 1, wherein the shank (20), together with the bristles (22), is produced by a milling method.

3. The cleaning instrument according to claim 2, wherein the milling method is a micro-milling method.

4. The cleaning instrument according to claim 1, wherein the shank (20), together with the bristles (22), is produced by a moulding method.

5. The cleaning instrument according to claim 4, wherein the moulding method is a micro-injection-moulding method.

6. The cleaning instrument according to claim 1, wherein the stiffening material comprises metal.

7. The cleaning instrument according to claim 1, wherein the bristles (22) overall form a substantially conical outer shape in the cleaning portion (14).

8. The cleaning instrument according to claim 1, wherein the bristles (22) are distributed over the outer surface of the shank (20) in a helical arrangement.

9. The cleaning instrument according to claim 1, wherein the bristles (22) are coated.

10. The cleaning instrument according to claim 9, wherein the bristles (22) are coated with an abrasive material or a chemically acting agent.

11. The cleaning instrument according to claim 10, wherein the abrasive material or the chemically acting agent comprises a cleaning agent, a disinfecting agent or a lubricating agent.

12. The cleaning instrument according to claim 1, wherein bristles (22a, 22b) project out from a tip of the shank (20) in substantially the same direction as the longitudinal axis of the shank (20).

13. A method of producing a cleaning instrument, for a tooth root canal, the cleaning instrument having a head portion (12) and, adjacent thereto, a cleaning portion (14) having a shank (20), the shank having an external surface which is provided with bristles (22) and a longitudinal axis, comprising the step of producing the shank (20) integral with the bristles (22), wherein the shank has a core (18) made from a stiffening material, wherein the shank (20) has a substantially conical shape and which symmetrically surrounds the core (18), and wherein the bristles (22) are arranged, at least in part, inclined towards the longitudinal axis of the shank and wherein the bristles (22) protrude from the shank (20) in a substantially perpendicular direction.

14. The method according to claim 13, wherein the producing step comprises milling the shank (20) together with the bristles (22).

15. The method according to claim 14, wherein the milling is micro-milling.

16. The method according to claim 13, wherein the producing step comprises moulding the shank (20) together with the bristles (22).

17. The method according to claim 16, wherein the moulding is micro-injection-moulding.

* * * * *